United States Patent [19]

Nozaki

[11] 4,306,189

[45] Dec. 15, 1981

[54] ANODE DEPLETION DETECTOR

[75] Inventor: Michio B. Nozaki, La Grange, Ill.

[73] Assignee: Rheem Manufacturing Company, New York, N.Y.

[21] Appl. No.: 70,346

[22] Filed: Aug. 27, 1979

[51] Int. Cl.³ .............................................. G01N 27/42
[52] U.S. Cl. ........................................ 324/425; 324/54
[58] Field of Search .................. 324/54, 425, 111, 96, 324/65 CR, 65 R

[56] References Cited

U.S. PATENT DOCUMENTS

| | | | |
|---|---|---|---|
| 2,607,528 | 8/1952 | McWhirter et al. | 324/111 |
| 2,843,839 | 7/1958 | Cunningham et al. | 324/111 |
| 2,872,642 | 2/1959 | Brewning | 324/111 |
| 3,351,545 | 11/1967 | Heuze | 324/425 |
| 3,405,041 | 10/1968 | Van Langermeersch | 324/425 |
| 4,087,742 | 5/1978 | Khoo | 324/65 CR |
| 4,096,435 | 6/1978 | Sabe | 324/96 |
| 4,114,990 | 9/1978 | Mash et al. | 324/96 |

*Primary Examiner*—Michael J. Tokar
*Attorney, Agent, or Firm*—Allegretti, Newitt, Witcoff & McAndrews

[57] ABSTRACT

An anode depletion detector includes a current carrying probe member which projects into a water heater tank. The probe is normally connected with electric energy storage means which is charged during contact with the probe. To test the level of anode protection, electric energy from the storage means is discharged through a detector. Alternative embodiments for circuits which permit storage and discharge of electrical energy are shown.

10 Claims, 6 Drawing Figures

ANODE DEPLETION DETECTOR

BACKGROUND OF THE INVENTION

This invention relates to an anode depletion detector particularly useful for hot water heater tanks.

Conventional gas or electric model hot water heaters do not have adequate mechanisms to monitor anodic protection devices for the glass coated, steel water tank. That is, the main body of a water heater is typically a steel vessel with a protective glass coating on the inside. Although the glass coating is nearly complete in its coverage of the inside surface of the tank, minute uncovered areas generally exist. These areas require protection against corrosion caused by hydrolysis.

It is known that a sacrificial anode installed within such a tank sufficiently protects the steel body by virtue of the galvanic reaction of the anode. Metals suitable as anode materials include aluminum, magnesium, zinc and zinc alloys. All of these metals rank higher in the ionization scale than steel.

When an anode material is present within the vessel of a water heater, the metal forms a positive pole or anode. The steel tank forms a negative pole or cathode. The constant flow of electric current from the positive anode metal to the steel body insures that the body will remain chemically inactive.

In such a system the direct current potential near the surface of a steel body must be at least 0.78 volts or greater. In practice, by use of the anode materials referenced above, the potential is maintained in the range of 1 to 1.5 volts so that a clearly sufficient tank protection is provided.

While the steel vessel is protected, the anode material is electrolytically consumed and transformed into oxides and hydroxides which settle at the bottom of the tank in a form of scale or are discharged with hot water. Finally, the anode material is totally depleted. When this happens the water heater tank is no longer protected and rust corrosion starts. Soon thereafter the tank may fail. When a tank is about to fail there is no prior indication. Rather the tank fails catastrophically, often causing total loss of hot water supply and water damage.

To avoid this experience, monitoring of the condition of a water heater is a desirable feature. In particular, it is desirable to monitor the condition of the anode material. This can be done by removing the anode material, which usually comprises a rod, from the water tank and making a visual inspection. Alternatively, a regular schedule for replacement of the anode material may be established. These procedures are, however, not easy. A special large socket wrench is normally required to unscrew the anode from a tank. The anode is normally not readily accessible. For example, head room to remove the anode is often not sufficient. All of these factors make it difficult to monitor the condition of an anode. For these reasons, such monitoring is normally ignored.

Therefore, a way to monitor the viability of an anode within a hot water heater tank in a convenient, simple and inexpensive manner has long been sought. The present invention constitutes a device which accomplishes this objective.

SUMMARY OF THE INVENTION

The present invention comprises a current carrying probe which projects into the fluid storage tank, generally a water heater tank. Electrical energy storage means are provided as are indicator means which are responsive to electrical energy discharge. A switch is provided to alternately provide for connection of the probe means to the electric storage means and the storage means to the indicator means. In this manner the storage means accumulates electrical energy when connected to the probe means. This electrical energy is discharged through the indicator means to provide an indication of the anodic current protection level within the storage tank. If the level is sufficient, then the anode need not be replaced. Both deficient and sufficient anode condition are detected by the device.

Thus it is an object of the present invention to provide an improved anode depletion detector for a fluid storage tank.

Another object of the present invention is to provide an improved anode depletion detector which measures the anode current level and provides a visual indication of that current level by indicator means.

Still another object of the present invention is to provide an anode depletion detector which is simple in construction, inexpensive, easy to manufacture and easy to install and service.

A further object of the present invention is to provide an anode depletion detector for a fluid storage tank which may be incorporated with the tank and which utilizes a minimum of space within the tank.

These and other objects, advantages and features of the present invention will be set forth in the detailed description which follows.

BRIEF DESCRIPTION OF THE DRAWING

In the detailed description which follows, reference will be made to the drawing comprised of the following figures.

DESCRIPTION OF THE PREFERRED EMBODIMENT

Figure 1:
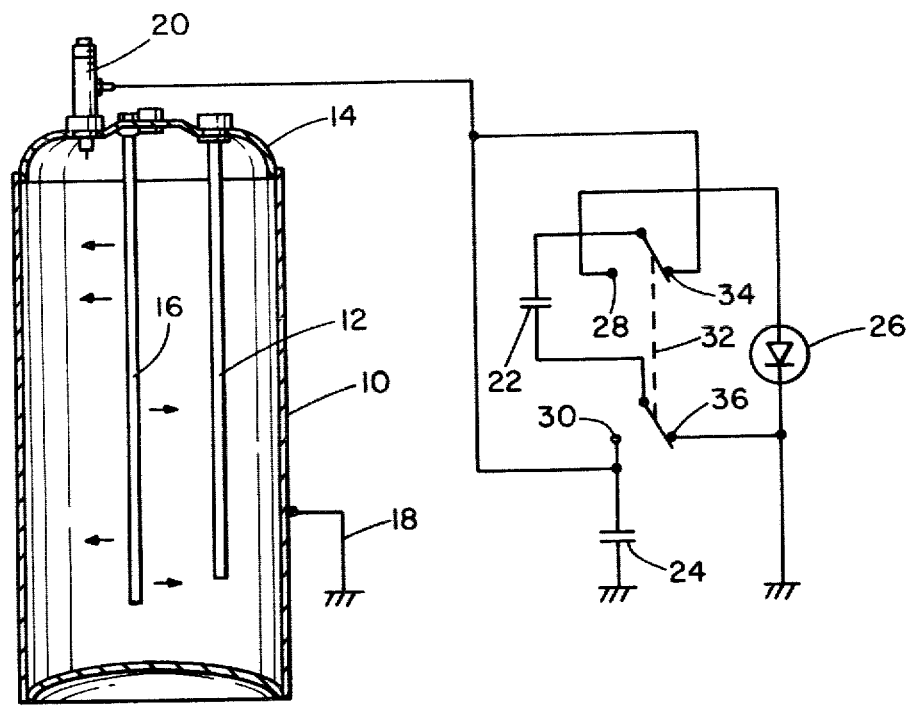
FIG. 1 is a schematic view of the electrical circuitry coupled with a cross sectional view of the improved detector of the present invention.

Referring to FIG. 1, a typical hot water tank or vessel 10 includes a cold water inlet pipe 12 projecting through a cap 14 to the bottom of tank 10. A magnesium anode or anode of similar known material in the form of a rod 16 also is mounted in the cap 14 and projects into the interior of the tank 10. The tank 10 is generally made from steel, is glass lined and is filled with water provided through the pipe 12. Water is removed from the tank 10 through a hot water outlet.

The probe 20 is comprised of a nipple 50 cooperative with hot water outlet fitting 52. Nipple 50 is threaded to the fitting 52. A plastic liner 54 fits within and lines the nipple 50. Liner 50 extends into the tank 10 and surrounds a metal probe rod 56. The conductive metal probe rod 56 is supported so as to project through an opening 58 in the nipple 50 and into tank 10. The probe rod 56 is mechanically and electrically sealed in the opening 58 by means of a rubber seal 60 and plastic washer 62. An electrical connector 64 connects the rod 56 electrically with a lead wire 66 attached to a detector switch and circuitry enclosed within a detector box 70. The tank 10 is grounded by ground wire or connection 18. The cooperative relationship of anode 16 and ground 18 ensure galvanic protection for the tank 10.

The anode depletion detector includes a probe 20 which attaches to the hot water outlet fitting 52 and projects through cap 14 into the water or fluid within the tank 10. A connecting wire 66 from the probe 20 connects with energy storage means and, more particularly, with capacitors 22 and 24 which are arranged in parallel and connected to ground.

Indicator means, for example, a light emitting diode 26 (LED) are arranged in association with normally open contacts 28 and 30 of double pole, double throw switch 32. The double pole, double throw switch 32 is preferably a momentary contact or spring loaded switch.

Normally the parallel capacitors 22 and 24 are simultaneously charged as a result of the connection with the probe 20. Each of the capacitors 22 and 24 are normally charged to a voltage in the range of 1.0 to 1.5 volts which is the anodic voltage as detected by the probe 20 projecting into the tank 10. Once the capacitors 22 and 24 are charged, current flow ceases and there is no further current draw from the anode 16.

To test the system shown in FIG. 1 and verify that the anode 16 is working in the designed and proper manner, the momentary switch 32 is depressed. Normally closed contacts 34 and 36 are then opened and a circuit is created through normally opened contacts 28 and 30. The capacitors 22 and 24, which were originally in parallel, are now arranged in series and the electrical energy or charge in the capacitors 22, 24 is discharged to ground through the light emitting diode 26. This causes a momentary emission of a bright light which is visible and sufficient to indicate the presence of adequate protection voltage within the tank 10.

Upon release of the switch 32, the switch 32 assumes the normally closed contact position as illustrated in FIG. 1. This permits the capacitors 22 and 24 to recharge. Of course, in the event there is a complete depletion of the anode 16, there will be no anode protection potential and the capacitors 22 and 24 will not be charged, nor will the light emitting diode 26 be activated upon operation of switch 32.

Figure 1A:
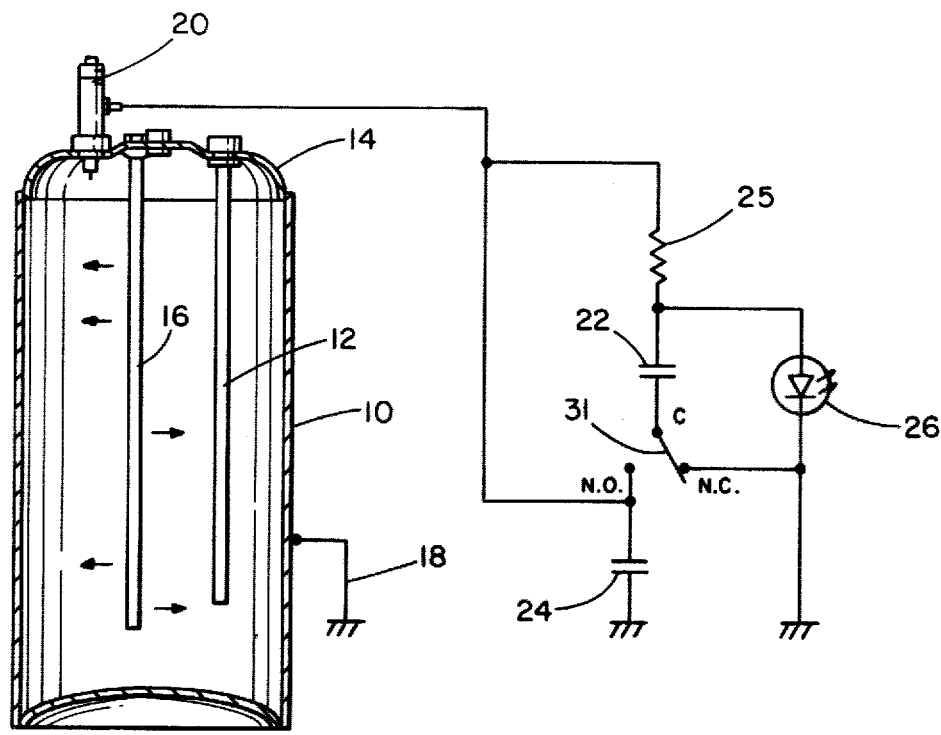
FIG. 1A is a schematic view of an alternative electrical circuit for the detector of FIG. 1.

FIG. 1A illustrates an alternative electric circuit and detector arrangement similar to that of FIG. 1 wherein the light emitting diode 26 is arranged in combination with the two capacitors 22 and 24, a resistor 25 and a single pole, double throw switch 31. The circuit of FIG. 1A is operative in combination with a resistor of approximately 10,000 ohms. Thus, since the light emitting diode 26 requires a forward bias voltage of more than 1.5 volts, the light emitting diode 26 may remain in the circuit without the loss of charge current and potential in any capacitors 22, 24. The light emitting diode 26 remains nonconductive during the capacitor charging cycle as shown in FIG. 1A. Since the charge current flow is of the order of 100 microamps or less, the resistor 25 offers very little impedance in the circuit. This permits the capacitor 22 to be charged when the circuit is in the switch position shown in FIG. 1A. By closing the normally closed switch 31 to the open position, the capacitors 22 and 24 both will discharge through the diode 26 thereby activating the diode 26. The resistor 25 acts as a high impedance path which prevents leakage of current and thus diverts all of the charge through the diode 26.

Figure 2:
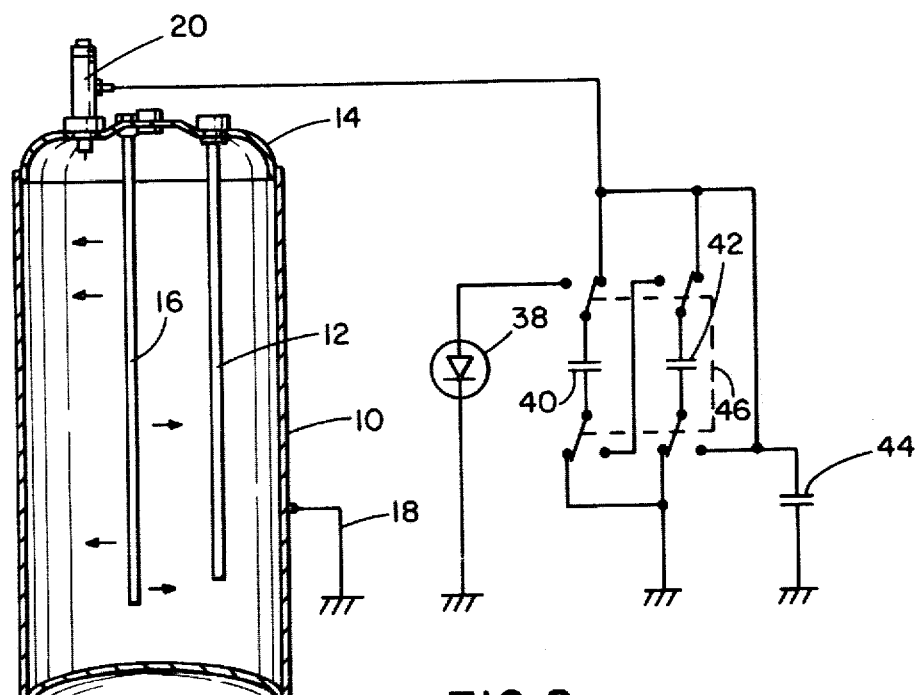
FIG. 2 is a combined schematic and cross sectional view of an alternative embodiment of the detector of the present invention.

FIG. 2 illustrates a circuit and detector arrangement substantially the same as that of FIG. 1 except that the detector comprises a liquid crystal diode 38 (LCD). Since the potential to operate a liquid crystal diode 38 is normally greater than that required for a light emitting diode, an additional capacitor is required. Thus, three capacitors 40, 42 and 44 are arranged to be in parallel when connected directly with the probe 20 and are arranged in combination with a switch 46 to be in series when connected with the liquid crystal diode 38. The switch arrangement, in effect, multiplies the driving voltage for the liquid crystal diode 38.

Figure 2A:
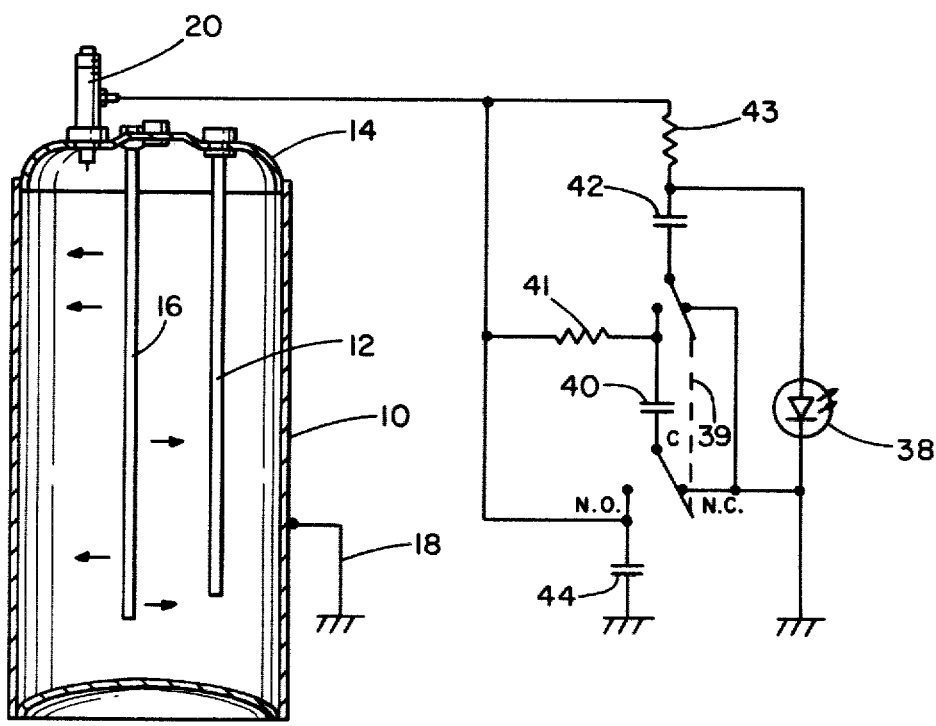
FIG. 2A is a schematic view of an alternative electric circuit for the detector of FIG. 2.

FIG. 2A illustrates an alternative circuit and detector arrangement for the circuit shown in FIG. 2. In the arrangement of FIG. 2A, a double pole, double throw switch 39 has been substituted for the four pole, double throw switch 46 of FIG. 2. First and second resistors 41 and 43 have been added to the circuit in a manner analagous to resistor 25 in FIG. 1A. In this manner, again, the impedance associated with the resistors 41 and 43 insure that the capacitors 40 and 42 will be charged during the switching configuration shown in FIG. 2A. Operation of the switch 39 will then provide for maintenance for a voltage sufficient to operate the liquid crystal diode 38. Clearly various other alternative circuit arrangements may be devised to provide for similar operation of the diodes 26 or 38.

Figure 3:
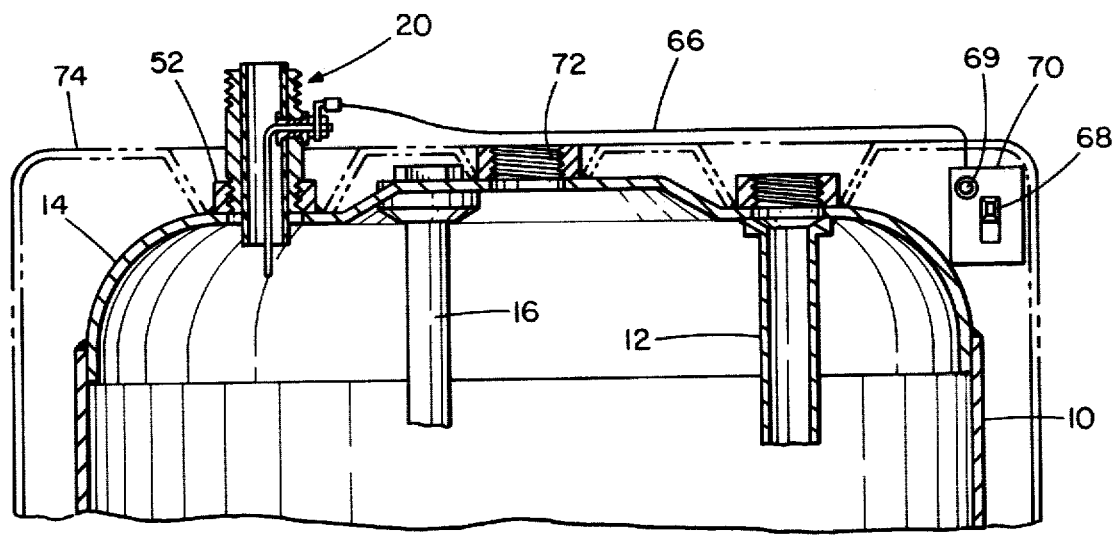
FIG. 3 is an enlarged cross sectional view of a portion of a hot water heater tank incorporating the improved detector of the present invention.
Figure 4:
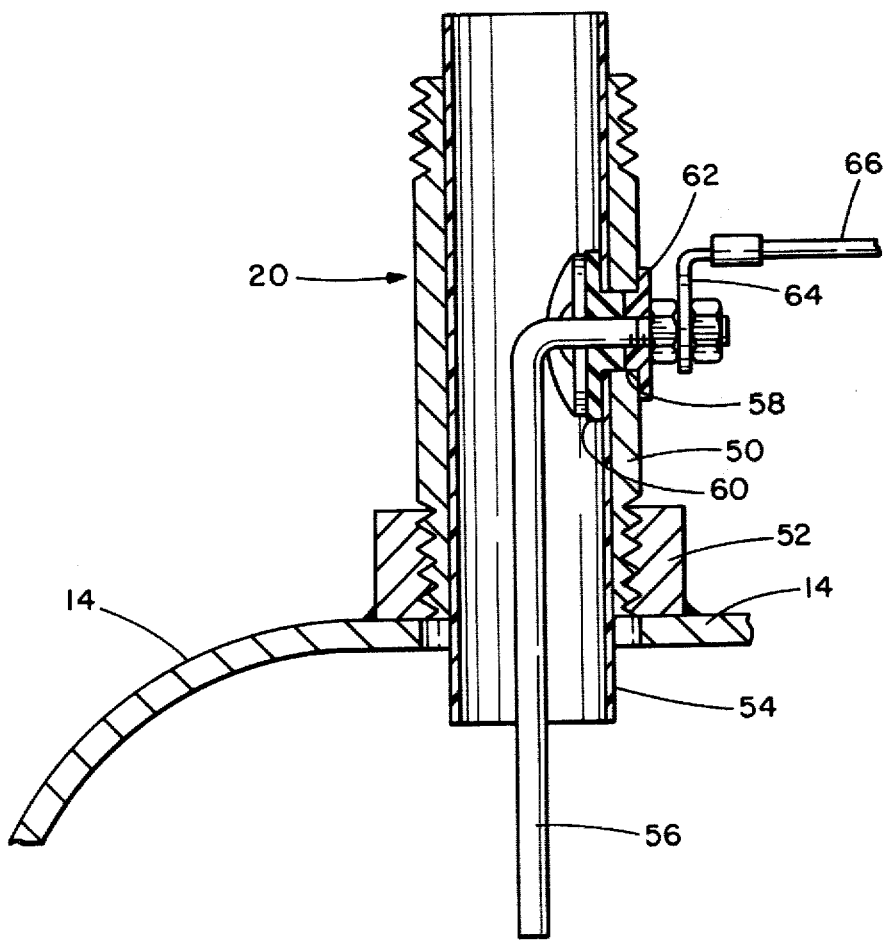
FIG. 4 is an enlarged cross sectional view of the probe mechanism associated with the anodic detector of the present invention.

FIGS. 3 and 4 illustrate in greater detail the structure of the detector of the present invention. Tank 10 includes a pressure and temperature relief valve opening 72 in the cap 14. A jacket 74 for the tank is shown in phantom in FIG. 3. The light emitting diode 26 or the liquid crystal diode 38 comprises an indicator means 69 in detector box 70.

While there has been set forth a preferred embodiment of the invention, it is to be understood that the invention is to be limited only by the following claims and their equivalents. Alternate constructions with respect to the invention and variations include replacement of the indicator means by various meters such as a volt meter or milliammeter are possible. The capacitors could be replaced by rechargeable batteries to act as an energy storage means. Other equivalent structures will be evident to those skilled in the art.

What is claimed is:

1. An anode depletion detector for a fluid storage tank comprising, in combination:
   a current carrying probe projecting into the fluid storage tank;
   electrical energy storage means for collecting a fixed charge of electrical energy;
   an indicator responsive only to a discharge of at least said fixed charge of electrical energy therethrough; and
   switch means for alternately (1) connecting the probe to the storage means and causing accumulation of electrical energy by the storage means and (2) connecting the storage means to the indicator and causing discharge of said collected energy from the storage means through the indicator when at the sufficient level to activate the indicator means and provide an indication of the anodic protection in the storage tank.

2. The detector of claim 1 wherein said storage means is charge storage means.

3. The detector of claim 1 wherein said storage means is capacitor means.

4. The detector of claim 1 wherein said indicator means is a liquid crystal diode.

5. The detector of claim 1 wherein said indicator is a light emitting diode.

6. The detector of claim 1 in combination with a water heater tank having a sacrificial anode.

7. The detector of claim 1 including means for insulating the probe from the tank.

8. The detector of claim 1 wherein said storage means comprise a plurality of capacitors in parallel when connected to the probe and in series when connected to the indicator, the collected potential change in the capacitors in series exceeding the sufficient level to activate the indicator.

9. The detector of claim 8 including double pole, double throw switch means for connecting the capacitors sequentially to the probe and indicator.

10. In a water heater of the type including a glass lined steel tank, an anode projecting into the tank, the improvement of an anode depletion detector comprising, in combination:

a charge activated indicator responsive only to a sufficient charge;

capacitative storage means capable of storing a cumulative charge of a fixed amount at least equal to the sufficient charge to activate the indicator;

an electrical circuit alternately connectable (1) between the anode and ground through the storage means and (2) between the storage means and indicator causing the storage means to be changed when the anode provides anodic protection and for discharging the charge through the indicator and activating the indicator only when the charge is a sufficient charge.

* * * * *